United States Patent
Jacob et al.

(10) Patent No.: US 7,229,412 B2
(45) Date of Patent: Jun. 12, 2007

(54) VIEWING SYSTEM HAVING MEANS FOR PROCESSING A SEQUENCE OF ULTRASOUND IMAGES FOR PERFORMING A QUANTITATIVE ESTIMATION OF FLOW IN A BODY ORGAN

(75) Inventors: Marie Jacob, Paris (FR); Olivier Gerard, Viroflay (FR); Antoine Collet-Billon, Paris (FR)

(73) Assignee: Koninklijke Philips Electronics N.V., Eindhoven (NL)

( * ) Notice: Subject to any disclaimer, the term of this patent is extended or adjusted under 35 U.S.C. 154(b) by 494 days.

(21) Appl. No.: 10/499,938

(22) PCT Filed: Dec. 11, 2002

(86) PCT No.: PCT/IB02/05356

§ 371 (c)(1),
(2), (4) Date: Jun. 23, 2004

(87) PCT Pub. No.: WO03/060553

PCT Pub. Date: Jul. 24, 2003

(65) Prior Publication Data
US 2005/0165308 A1 Jul. 28, 2005

(30) Foreign Application Priority Data
Dec. 28, 2001 (EP) .................. 01403392

(51) Int. Cl.
*A61B 8/00* (2006.01)
(52) U.S. Cl. ..................................... 600/454
(58) Field of Classification Search ........ 600/437–472; 128/916
See application file for complete search history.

(56) References Cited

OTHER PUBLICATIONS

"Hemielliptic Proximal Isovelocity Surface Area Method Modified for Clinical Application, More Accurate Quantification of Mitral Regurgitation In Doppler Echocardiography" by Hiroko Fuji et al., in Japanese Circulation Journal, vol. 65, Sep. 2001, pp. 820-826.

"Simplex Meshes: a General Representation for 3D shape Reconstruction" published in the "Proceedings of the International Conference on Computer Vision and Pattern Recognition (CVPR'94), Jun. 20-24, 1994, Seattle, USA".

*Primary Examiner*—Ali Imam

(57) ABSTRACT

A medical ultrasound viewing system for processing a sequence of three-dimensional (3-D) ultrasound images far performing a quantitative estimation of a flow through a body organ comprising means for performing steps of acquiring a sequence of 3D color flow images, of said flow; assessing the flow velocity values in the 3D images, constructing isovelocity surfaces (6) by segmentation of the flow velocity values; computing the volume (Vol) delimited by the isovelocity surfaces; and using the flow velocity value (V) and the volume (Vol) computed from a segmented surface for computing the surface of an orifice (3) of the organ through which the flow propagates. The viewing system further comprises means for performing steps of measuring the peak velocity ($V_{REG}$) of said flow through said orifice; computing the surface of the orifice (SOR) through which the flow propagates as a function of the flow velocity value (V) at an isovelocity surface upstream the flow propagation with respect to said orifice, the volume (Vol) computed from said segmented isovelocity surface, and the peak velocity of the flow through said orifice. The surface is given by the formula: SOR=Vol. $V/V_{REG}$. The system can be applied to the assessment of the surface of regurgitation of the mitral jet.

13 Claims, 2 Drawing Sheets

VIEWING SYSTEM HAVING MEANS FOR PROCESSING A SEQUENCE OF ULTRASOUND IMAGES FOR PERFORMING A QUANTITATIVE ESTIMATION OF FLOW IN A BODY ORGAN

CROSS-REFERENCE TO RELATED APPLICATIONS

This application claims priority from the pending International Patent Application PCT/IB02/05356 filed on Dec. 11, 2002, and from the pending European Patent Application 01403392.2 filed on Dec. 28, 2001.

FIELD OF THE INVENTION

The invention relates to a viewing system having means for processing a sequence of three-dimensional (3-D) ultrasound images for performing a quantitative estimation of a flow in a body organ. In particular, the invention relates to a medical viewing system and to an image processing method for performing an automatic quantitative estimation of the blood flow through the heart valves, and/or of the regurgitant jet, from a sequence of 3-D color flow images.

The invention particularly finds an application in the field of medical imaging in cardiology using ultrasound medical apparatus and/or viewing systems.

BACKGROUND OF THE INVENTION

A method for assessing mitral regurgitation is already known from the publication entitled "Hemielliptic Proximal Isovelocity Surface Area Method Modified for Clinical Application, More Accurate Quantification of Mitral Regurgitation In Doppler Echocardiography" by HIROKO FUJI et al.", in Japanese Circulation Journal, Vol. 65, September 2001, pages 820-826. According to this publication, the Proximal Isovelocity Surface Area (PISA) method is used for quantitative estimation of the mitral jet regurgitation. The PISA shape is chosen hemielliptic rather than hemispheric on a slit-like orifice, because the hemielliptic method is more accurate than the hemispheric method for in vitro studies. Nevertheless, the hemispheric method is used clinically because of its simplicity, whereas the hemielliptic method is difficult to approach from 3 orthogonal directions. The publication in reference presents a modified approach for use in clinical applications. A closed circuit, constant flow system was designed to simulate PISA, and various types of slit-like orifices were selected. Three orthogonal PISA radii were measured and flow rates were calculated using the original hemielliptic formula using the three orthogonal PISA radii. Flow rates were also calculated indirectly using a linear regression formula, and PISA radii from a bird's eye approach and lateral approaches (modified hemielliptic method) were compared. Flow rates that were determined using the original hemielliptic method correlated significantly with actual flow rates. Similarly, flow rates calculated using the modified hemielliptic method correlated significantly with actual flow rates. So, the study results imply that the proposed modified hemielliptic method could be used in clinical applications.

SUMMARY OF THE INVENTION

The quantitative estimation of the blood flow through the heart valves, from 3D color flow image sequences, has important clinical implications for the assessment of the condition of the valves. The estimation of the importance of the regurgitant jet is an index of the severity of the valve diseases, such as the congenital malformation or the valvular insufficiency, or the lack of attachment of the chordal structures. The presence of a normal regurgitation is also very often to be found in non-pathologic patients. This normal regurgitation is used to estimate the pressure in the cavities, for instance in the case of patients suffering from hypertension. Also, the study of the flow through the valve helps the diagnosis in case of a stenosis of the cardiac valves. The intracardiac blood flow is also studied in the follow-up of valve transplants comprising estimation of the residual regurgitation, detection and quantification of the para-prosthetic leaks that can cause the disinsertion of the prosthesis.

Recent years have seen the introduction of a high quality imaging modality which uses the Doppler shift for the study of blood flow and tissue motion. 2-D color Doppler ultrasound technology has now reached a level of maturity. Combined with gray level exam, this is the most widely used technique for assessing valve diseases. Several methods based on this 2-D image processing technique are known for estimating the severity of the regurgitation. These methods are based on measurements on the cross-sectional jet that can be the length of the jet, or its area. However, these measurements, even though they are based on the maximal demonstrable regurgitant jet, tend to underestimate the extent of the jet. Scanning multiple planes only reduces this underestimation. These measurements can also vary considerably over consecutive repeated measurements, because they depend on the choice of the image plane. Moreover, the regurgitant jet can be eccentric or asymmetric, and can reverberate against the heart walls, which is the case in most severe mitral regurgitations for instance, and which does not permit of assessing the actual mitral regurgitation correctly. Hence, on the one hand, the known 2-D measurements do not permit of quantifying said mitral regurgitation accurately. That is why the emergent 3-D color Doppler technique, based on the 3-D reconstruction of the color flow, is considered as the future reference method for assessing valve diseases severity. However, on the other hand, the publication by HIROKO FUJI et alii, in reference, which is based on geometrical assumption limited to a very strict hemielliptic shape of the isovelocity surface of the 3D color flow of the blood issuing the mitral valve, does not permit of reaching sufficiently accurate results. This shows the need for more accurate tools to automatically quantify the severity of the regurgitation in 3-D color Doppler images.

The invention has for an object to provide a viewing system associated to an ultrasound examination apparatus and an image processing method for performing an automatic quantitative estimation of a flow through a body organ, from a sequence of three-dimensional (3-D) ultrasound color flow images. According to the invention, a 3-D ultrasound technique is used for acquiring a sequence of 3-D color flow images of a flow through an orifice, for instance using a 3-D color Doppler technique, within an interval of time. Then, a map of isovelocity surfaces is constructed by velocity segmentation related to the blood flow at the vicinity of said orifice, issuing through the orifice, which permits of estimating both the blood velocity at a given surface and the actual volume delimited by said isovelocity surface. The peak velocity of the regurgitant jet of blood through the orifice, in the opposite direction, is also measured using a pulse wave Doppler technique. These measured data permit of calculating the surface of the orifice. In particular, for estimating the severity of the mitral regurgitation through the heart valve, the Surface Of Regurgitation (SOR) can be obtained by calculations based on the real volume corresponding to the real PISA.

Such a viewing system is claimed in claim 1. Particular embodiments of the viewing system, an examination apparatus associated to the viewing system and an image processing method to be carried out in the system, are claimed in dependent claims.

BRIEF DESCRIPTION OF THE DRAWINGS

The invention is described hereafter in detail in reference to the following diagrammatic drawings, wherein.

DESCRIPTION OF THE PREFERRED EMBODIMENTS

The invention relates to a viewing system for performing a quantitative estimation of a flow in a body organ. In particular, the invention relates to a medical viewing system and to an image processing method for performing an automatic quantitative estimation of the blood flow through the heart valves, and/or of the regurgitant jet, from a sequence of 3-D color flow images.

The method can be carried out using reconstructed or real-time 3D echocardiography, the images being formed using a trans-thoracic or a trans-esophageal probe. The method of the invention can also be applied to a sequence of 3-D images of other organs of the body that can be formed by ultrasound systems or ultrasound apparatus, or by other medical imaging systems known of those skilled in the art.

In the example described hereafter, severity of the cardiac regurgitant jet between the left heart atrium and the left heart ventricle is assessed from a sequence of 3-D Doppler color flow images.

Figure 1:
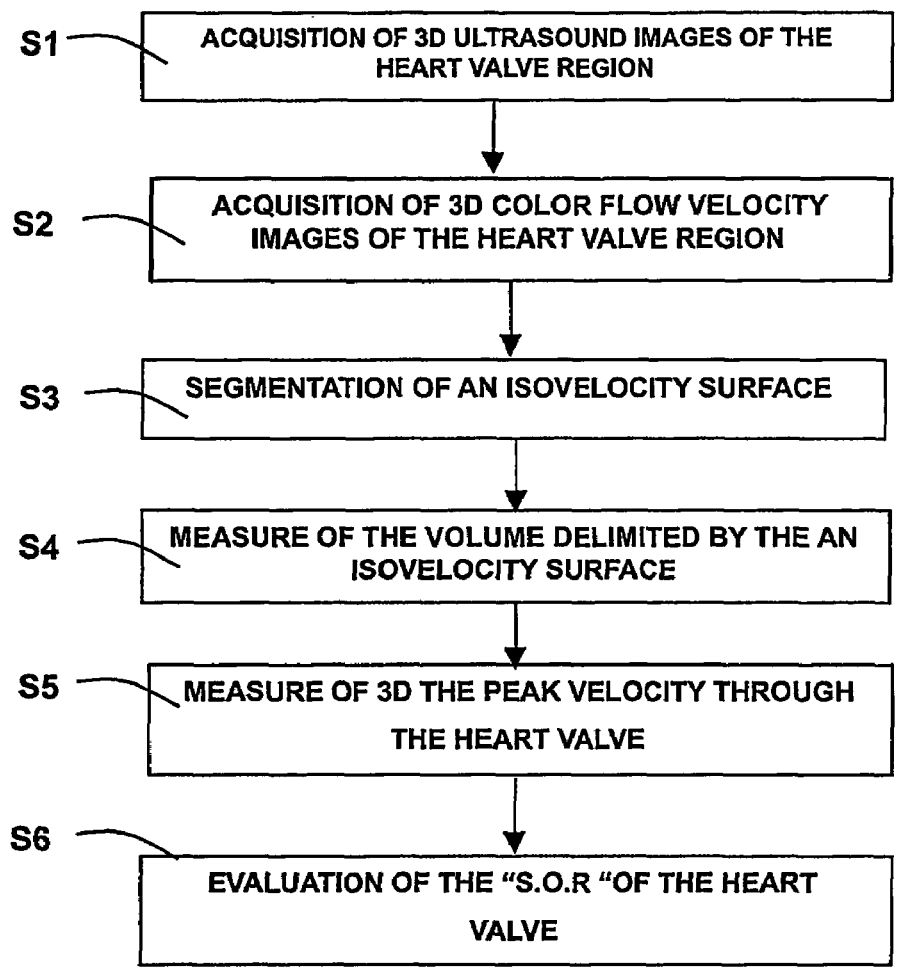
FIG. 1 is a flow chard of the functions performed by the viewing system.

Referring to FIG. 1, the ultrasound examination apparatus yields ultrasound data to the viewing system. In a step S1, the viewing system acquires a sequence of 3D ultrasound images of the heart atrium, the heart left ventricle and the mitral valve, which is located between the left atrium and the left ventricle, during an interval of time, for instance between two heart pulses. The sequence images can be acquired at a rate of 15 to 30 or 50 images per second, each image of the sequence being preferably associated to an instant of the cardiac cycle. Other examples of forming sequences of 3-D images of different organs may be found by operators of ultrasound apparatus or of other systems of image acquisition.

Figure 3:
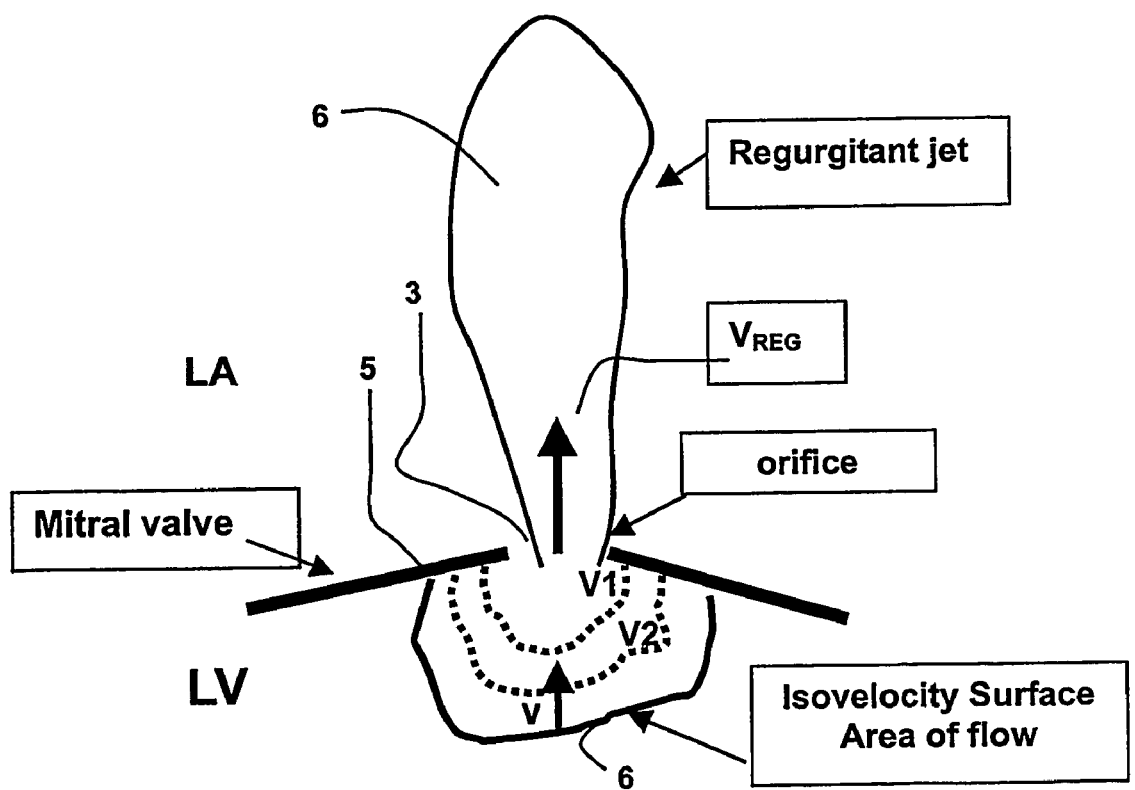
FIG. 3 illustrates the determination of the Surface Of Regurgitation "S.O.R"

In a step S2, the viewing system acquires a sequence of 3D Doppler color flow velocity images of the blood flow normally issuing from the heart atrium, and entering the heart left ventricle through the mitral valve. Referring to FIG. 3, when a disease of the heart does not permit the mitral valve to completely close at given heart pulse instants, then a regurgitant jet retropropagates from a small remaining orifice 3 let by the mitral valve 5 toward the atrium, in the opposite direction with respect to the normal direction of blood flow. The invention has for an object to provide a quantitative measure relative to the severity of the regurgitant jet.

In a step S3, the viewing system has segmentation means to construct 3D isovelocity surfaces from the Doppler color flow images. In case of normal functioning of the heart, each of these surfaces yields the blood velocity value in the normal direction of the blood flow, i.e. in the conventional blood direction from the left atrium LA to the left ventricle LV. It is to be noted that, due to the existence of a remaining orifice 3 of the mitral valve 5, isovelocity surfaces that are inside the left ventricle LV, near said remaining orifice of mitral valve 5, concern the velocity of the blood flow that leaves the left ventricle opposite to the conventional blood direction, through said remaining orifice, and that contributes to form the regurgitant jet. These isovelocity surfaces concern the velocity of an upstream flow with respect to said remaining orifice of the mitral valve that permits the existence of the regurgitant jet and with respect to the flow of said regurgitant jet. These isovelocity surfaces 6 of said upstream flow are constructed and shown in FIG. 3.

Several different possible technique of segmentation may be used for constructing said color flow isovelocity surfaces 6. The segmentation techniques allow to obtain surface models that are extremely near to the actual isovelocity surfaces and are not an approximation of the surfaces or an assumed geometrical shape of the surfaces, as was proposed by the state of the art. Since the isovelocity surfaces are not smooth, they cannot be estimated correctly by any assumed geometrical shape, because the assumed surface constitutes a too rough approximation. The segmentation technique is applied on the Doppler blood color flow data provided by step S2.

A first segmentation technique is already disclosed by H. Delingette in the publication entitled "Simplex Meshes: a General Representation for 3D shape Reconstruction" published in the "Proceedings of the International Conference on Computer Vision and Pattern Recognition (CVPR'94), 20-24 Jun. 1994, Seattle, USA". In this paper, a physically based approach for recovering three-dimensional objects is presented. This approach is based on the geometry of "Simplex Meshes". Elastic behavior of the meshes is modeled by local stabilizing functions controlling the mean curvature through the simplex angle extracted at each vertex (node of the mesh). Those functions are viewpoint-invariant, intrinsic and scale-sensitive. Unlike distortable surfaces defined on regular grids, Simplex Meshes are very adaptive structures. A refinement process for increasing the mesh resolution at highly curved or inaccurate parts is also disclosed. Operations for connecting Simplex Meshes in order to recover complex models may be performed using parts having simpler shapes. A Simplex Mesh has constant vertex connectivity. For representing 3-D surfaces, 2-D Simplex Meshes, where each vertex is connected to three neighboring vertices, are used. The structure of a Simplex Mesh is dual to the structure of a triangulation as illustrated by the FIG. 1 of the cited publication. It can represent all types of rotatable surface. The contour on a Simplex Mesh is defined as a closed polygonal chain consisting in neighboring vertices on the Simplex Mesh. The contour is restricted to not intersect itself. Contours are distortable models and are handled in independently of the Simplex Mesh where they are embedded. Four independent transformations are defined for achieving the whole range of possible mesh transformations. They consist in inserting or in deleting edges in a face. The description of the Simplex Mesh also comprises the definition of a Simplex Angle that generalized the angle used in planar geometry; and the definition of metric parameters that describe how the vertex is located with respect to its three neighbors. The dynamic of each vertex is given by a Newtorian law of motion. The deformation implies a force that constrains the shape to be smooth and a force that constrains the mesh to be close to the 3-D data-Internal forces determine the response of a physically based model to external constraints. The internal forces are expressed so that they be intrinsic viewpoint invariant and scale dependant. Similar types of constraints hold for contours. Hence, the cited publication provides a simple model for representing a 3-D object of interest. It defines the forces to be applied in order to reshape and adjust the model onto the 3-D object of interest. The "Simplex Mesh technique" is a robust segmentation technique.

A second possible segmentation technique is already disclosed in a publication entitled "A fast marching level set method for monotonically advancing fronts" by J. A. SETHIAN in Proc. Nat. Acad. Sci., USA, Vol. 93, pp. 1591-1595, February 1996, Applied Mathematics. According to said reference, a front, formed in a 2-D grid of potential values, is propagated using a "Fast Marching Technique" with a determination of the front points. The front is a solution of a so-called Eikonal Equation. The Fast Marching Technique introduces order in the selection of the grid points and sweeps the front ahead in one pass on the 2-D image. The Fast Marching Technique comprises marching the Front outwards by freezing already visited points denoted Alive, coming from a set of points referred to as Narrow Band, and by bringing new ones denoted Far Away into said Narrow Band. The Narrow Band grid points are always up-dated as those having minimal potential values in a neighboring structure denoted Min-Heap and the potential of the neighbors are further re-adjusted. Said Fast Marching technique provides one path of minimal cost joining a first end point called Start Point to respectively each point of the front, said front propagating until a second and final end point, called End Point is reached. It is interesting to note that the points of a path constructed in the operation of marching the front forwards are points, which have the smallest possible potentials. Starting at the Start Point, and going forwards from one point to the next point must be at the "minimal cost". So, such a path is a path of "minimal Action", i.e. a path on which the "Sum" or the "Integral" of potentials calculated over point potentials is the smallest though strictly continuously growing as a function of the number of points present on said path between the Start Point and the current point on the front. This Front Propagation Technique thus needs two End-Points between which it propagates the Front onwards and backwards. Referring to FIG. 3, according to the invention, the Start Point for propagating the front is set in the substantially middle of the orifice 3. The front has two End values, which are:

The value of the velocity V of the chosen isovelocity surface 6 of the upstream flow related to the regurgitant flow, with respect to the remaining orifice in the mitral valve 5; and The value of a velocity substantially near ZERO, which is the velocity at the vicinity of the mitral valve 5 itself.

The system has means to provide in step S4, accurate values of the velocity V at the surface of a given isovelocity surface model together with the actual volume, denoted by Vol, delimited by the considered isovelocity surface 6. This values V and Vol are calculated from the images of the Doppler color simplified models of the Doppler color flow isovelocity surfaces of said upstream flow, which are obtained from the segmentation of 3-D ultrasound Doppler color blood flow of the heart at the vicinity of the mitral valve of the heart as described for carrying out said previous step S4.

The system has means to perform a step S6, wherein the peak velocity of the regurgitant jet, denoted by $V_{REG}$, which is in the same direction as the velocity V of the isovelocity surface 6 of said upstream flow, is measured using a known technique of pulse wave Doppler.

Now the system has calculation means to perform a step S7 of calculating the surface, denoted by Surface Of the Regurgitant jet "S.O.R", of said remaining orifice 3 of the mitral valve 5 through which the regurgitant jet is emitted. This surface is calculated through the following formula:

$$SOR = Vol \times V/V_{REG}$$

This formula yields the surface value "S.O.R" with the minimum of approximation since the evaluation of the volume by surface segmentation is as near as possible of the actual volume.

The above-described method can be applied to any estimation of a surface of an orifice through which a flow of a fluid is emitted and propagates. The direction of the flow may be the conventional direction, or opposite to the normal direction usually found for the flow of said fluid.

The above-described method can be applied without difficulty to 2-D images, which are for instance cross-sections of the 3-D images of a 3-D object. In the case of the simplex mesh segmentation method, the 2-D segmented objects of the sequence are polygons. For a 3-D sequence of images, one might provide three orthogonal cross-section image sequences. When other segmentation methods are used, the 2-D images represent the trace of the wall of the segmented 3-D object.

The 3D or the 2D methods may be applied to ultrasound images as well as to X-ray images or to any other kind of image sequences.

Figure 4:
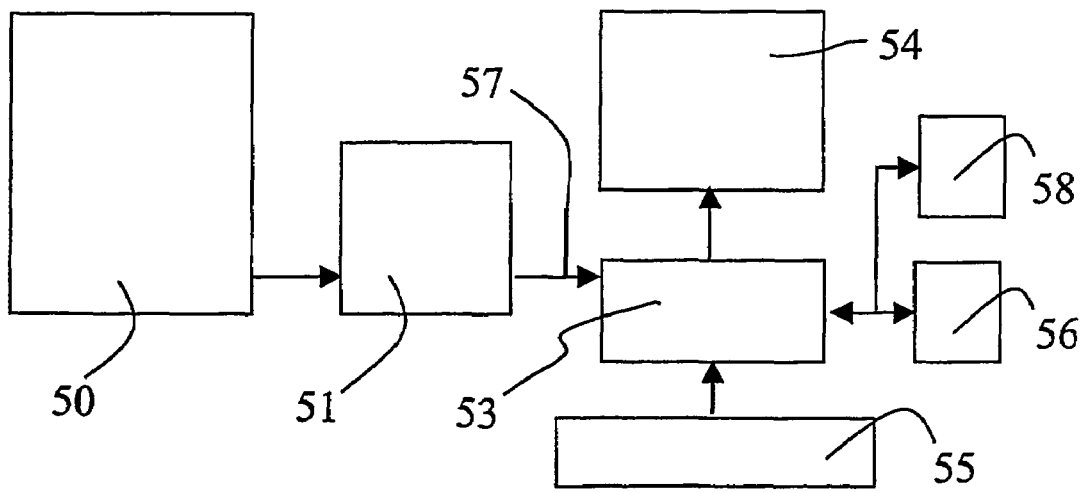
FIG. 4 shows a diagram of an ultrasound examination apparatus having a viewing system.
Figure 2:
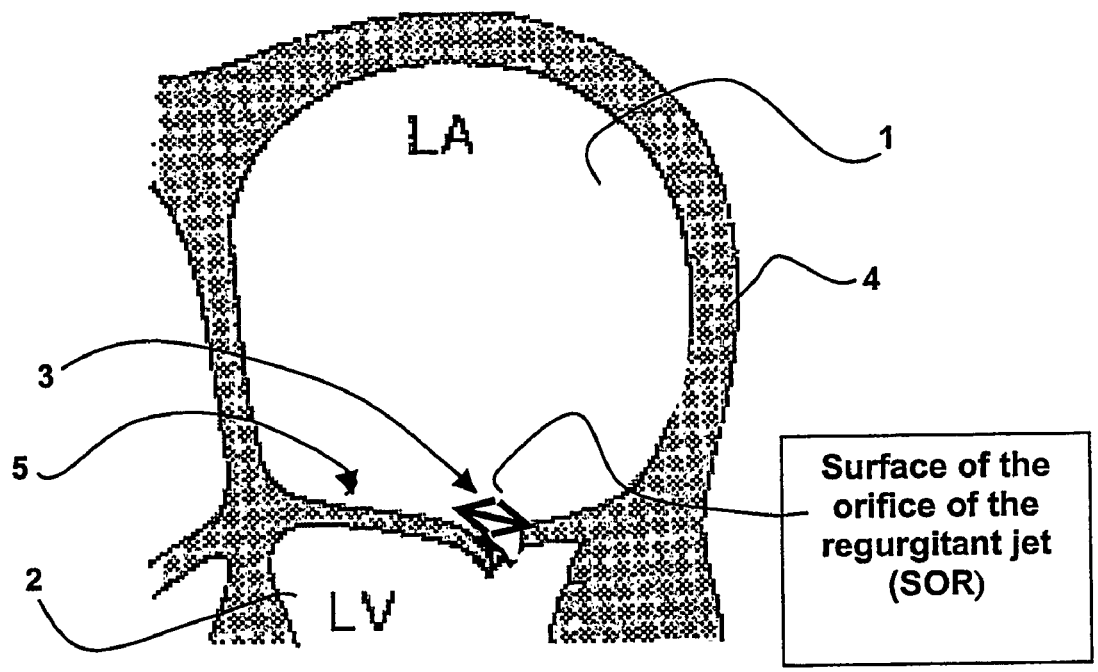
FIG. 2 shows a schematic drawing of the left atrium and left ventricle with a valve.

Referring to FIG. 4, a medical examination apparatus 150 comprises means for acquiring a digital image sequence, and a viewing system 120 for processing these data according to the processing steps above-described. The medical examination apparatus comprises means for providing image data to the viewing system 120, which has at least one output 106 to provide image data to display and/or storage means 130, 140. The display and storage means may respectively be the screen 140 and the memory 130 of a workstation 110. Said storage means may be alternately external storage means. This image viewing system 120 may comprise a suitably programmed computer of the workstation 110, or a special purpose processor having circuit means such as LUTs, Memories, Filters, Logic Operators, that are arranged to perform the functions of the method steps according to the invention. The workstation 110 may also comprise a keyboard 131 and a mouse 132. This medical examination apparatus 150 may be a standard ultrasonic apparatus. The viewing system 120 may use a computer program product having program instructions to be executed by the computing means of said processing system.

The invention claimed is:

1. A medical ultrasound viewing system for processing a sequence of three-dimensional (3-D) ultrasound images for performing a quantitative estimation of a flow in a body organ comprising means for performing steps of:
   acquiring a sequence of 3-D color flow images, of a flow in a body organ;
   assessing flow velocity values in the 3-D images,
   constructing isovelocity surfaces by segmentation of the flow velocity values;
   computing volume delimited by a surface of the isovelocity surfaces; and using the flow velocity value and the volume computed from said surface, for computing a surface of an orifice of the organ through which the flow propagates.

2. The medical ultrasound viewing system of claim 1, wherein the assessing step comprises measuring peak velocity of said flow into said orifice, and wherein the surface computing computes said surface of an orifice as a function of:

said flow velocity value;
said volume computed from said; and
the measured peak velocity.

3. The system of claim 2, wherein the technique of segmentation is an active mesh model technique.

4. The system of claim 2, wherein the technique of segmentation is a front propagation technique, whose starting values and stopping values are the velocities at the isovelocity surface.

5. The system of claim 2, wherein said surface computing comprises dividing a product of said volume and said flow velocity value by said measured peak velocity.

6. The system of claim 5, wherein the 3-D ultrasound images are acquired from the heart atrium, the heart left ventricle and the mitral valve, using blood flow color 3-D imaging for assessing mitral regurgitation, wherein said surface computing computes a surface of regurgitation of the mitral valve.

7. The system of claim 2, wherein said surface computing computes a volume, said system comprising means for selecting another of the constructed isovelocity surfaces based on the computed volume.

8. The system of claim 7, wherein said selecting selects said another surface by matching a volume delimited by said another surface to the computed volume.

9. An ultrasound examination apparatus having means to acquire medical image data, having a system as claimed in claim 1, having access to said medical digital image data, and processing the image data, and having means to display the processed images.

10. A computer program product comprising a set of instructions embodied within a computer-readable medium, said product for carrying out the steps as claimed in claim 1.

11. The system of claim 1, wherein said body organ is the heart, said orifice being formed and defined by a regurgitant jet embodying said flow through the mitral valve.

12. The system of claim 1, wherein the computed surface coincides with another of the constructed isovelocity surfaces.

13. A medical ultrasound method for processing a sequence of three-dimensional (3-D) ultrasound images for performing a quantitative estimation of a flow in a body organ comprising:

acquiring a sequence of 3-D color flow images, of a flow in a body organ; assessing flow velocity values in the 3-D images, constructing isovelocity surfaces by segmentation of the flow velocity values;

computing volume delimited by a surface of the isovelocity surfaces; and using the flow velocity value and the volume computed from said surface, for computing a surface of an orifice of the organ through which the flow propagates.

* * * * *